(12) United States Patent
Hamilton

(10) Patent No.: US 11,125,683 B2
(45) Date of Patent: Sep. 21, 2021

(54) SYSTEMS AND METHODS FOR MEASURING SPECTRAL ABSORPTION BY OBJECTS

(71) Applicant: Dukane IAS, LLC, St. Charles, IL (US)

(72) Inventor: Dax Hamilton, St. Charles, IL (US)

(73) Assignee: Dukane IAS, LLC, St. Charles, IL (US)

( * ) Notice: Subject to any disclaimer, the term of this patent is extended or adjusted under 35 U.S.C. 154(b) by 0 days.

(21) Appl. No.: 17/130,793

(22) Filed: Dec. 22, 2020

(65) Prior Publication Data

US 2021/0199569 A1    Jul. 1, 2021

Related U.S. Application Data

(60) Provisional application No. 62/953,700, filed on Dec. 26, 2019.

(51) Int. Cl.
| | | |
|---|---|---|
| *G01N 21/3563* | (2014.01) | |
| *G01N 33/207* | (2019.01) | |
| *G01N 21/88* | (2006.01) | |

(52) U.S. Cl.
CPC ..... *G01N 21/3563* (2013.01); *G01N 21/8806* (2013.01); *G01N 33/207* (2019.01)

(58) Field of Classification Search
CPC ............ G01N 21/3563; G01N 33/207; G01N 21/8806
USPC ................. 356/402–425, 600–613, 432–448
See application file for complete search history.

(56) References Cited

U.S. PATENT DOCUMENTS

| | | |
|---|---|---|
| 10,295,459 B1 | 5/2019 | Hamilton |
| 2004/0150688 A1 | 8/2004 | Kwan |
| 2006/0092412 A1* | 5/2006 | Doshoda ................. G01J 3/504 |
| | | 356/243.1 |
| 2007/0138465 A1* | 6/2007 | Li .......................... H01L 22/14 |
| | | 257/48 |

(Continued)

FOREIGN PATENT DOCUMENTS

| | | |
|---|---|---|
| DE | 10121923 A1 | 11/2002 |
| WO | WO 2011/018513 A1 | 2/2011 |

OTHER PUBLICATIONS

Extended European Search Report for Application No. 20216158.4, dated May 26, 2021 (7 pages).

*Primary Examiner* — Tri T Ton
(74) *Attorney, Agent, or Firm* — Nixon Peabody LLP

(57) ABSTRACT

Identifying object characteristic based on a contrast ratio of an amount of light reflected or absorbed by the object. Part of the object is illuminated, where the object is a material that absorbs or reflects light emitted by the light source. An amount of light absorbed/reflected by the object is measured. A contrast ratio of the absorbed/reflected light is determined by comparing an amount of light absorbed/reflected by the object to a default absorption or reflection value to obtain a difference between the amount of light absorbed/reflected by the object and the default absorption/reflection value. A characteristic of the object is determined based on the contrast ratio. The wavelength of the light from the light source can be substantially the same as the wavelength of the energy used to form the object by a welding process that uses energy to join at least two parts together to form the object.

30 Claims, 9 Drawing Sheets

(56) References Cited

U.S. PATENT DOCUMENTS

2007/0238033 A1* 10/2007 Kanayama ............. B82Y 40/00
                                                    430/5
2016/0363437 A1* 12/2016 Safai .................... G01N 21/954
2020/0393371 A1* 12/2020 Nishizawa ......... G01N 21/8914

* cited by examiner

SYSTEMS AND METHODS FOR MEASURING SPECTRAL ABSORPTION BY OBJECTS

CROSS-REFERENCE TO RELATED APPLICATIONS

This application claims the benefit of U.S. Provisional Application Ser. No. 62/953,700, filed Dec. 26, 2019, which is incorporated herein by reference in its entirety.

FIELD OF THE INVENTION

The present disclosure relates generally to non-destructive methods to determine weldability of parts welded together, and systems to accomplish the same.

BACKGROUND OF THE INVENTION

Objects undergo an inspection process prior to being used in order to ensure quality, aesthetics, and reduce the risk of failure. Objects of an aesthetic nature may be inspected for imperfections. Objects that are critical to an operation of a machine may be inspected for imperfections and defects to reduce or eliminate failure of the objects during the operation of the machine. When the imperfection or defect sought to be identified is a weld joint or welded area, conventional approaches are destructive and require cutting or slicing the object through the weld joint to visually inspect the weld quality, adjusting the weld settings if the weld joint is deemed to be sub-optimal, welding a new set of parts together using the adjusted weld settings, cutting and inspecting the new weld joint, and repeating this process until the weld quality is deemed to be satisfactory. This process is time-consuming and also requires subjective assessments by well-trained weld inspectors, which can be prone to human error and requires specialized training and experience.

BRIEF SUMMARY

The present disclosure describes a non-destructive, non-invasive way of objectively assessing and characterizing weld quality or "weldability" of parts without cutting or slicing them through the weld joint or requiring a human operator to visually assess weldability. It has been found that when infrared light is directed at the weld joint using a wavelengh that matches the wavelength of the energy (such as laser energy) used to weld the parts together, an objective comparison can be made without human intervention of the weldability of the parts. For example, when a 1 nm laser is used to weld the parts together, directing a 1 nm wavelength of infrared light at the weld joint produces an absorption pattern or signature that can be detected using an imaging device, and the pixel values indicative of the amount of absorption can be used as an index as to the weldability of the parts. Advantageously, adjustments can be made automatically to weld parameters or settings until the weld joint quality or weldability is within an optimal range, at which time the weld parameters used to produce such optimal weld joint can be set and used thereafter to weld multiple sets of parts together during manufacturing to produce repeatable and reliably consistent weld joints using those optimized weld parameters.

According to an aspect of the present disclosure, a method includes: illuminating, by a light source, an entire object. The light source is a laser emitting light at one micron. The light source includes a back plate that reflects light emitted through a bottom of the object. The object is a material that absorbs a portion of the light emitted by the laser. The method further includes measuring, by a sensor, an amount of light absorbed by the object, wherein the amount of light absorbed by the object is the amount of light not reflected by the object; determining, by a processing device, a contrast ratio of the absorbed light by comparing an amount of light absorbed by the object to a default absorption value to obtain a difference between the amount of light absorbed by the object and the default absorption value; determining, by the processing device, a characteristic of the object based on the contrast ratio; and providing a notification to a user indicating the characteristic of the object.

The default absorption value can be a value indicative of an amount of light absorbed by a first portion of the object. The amount of light absorbed by the object can be an amount of light absorbed by a second portion of the object. The contrast ratio can be a difference between the amount of light absorbed by the first portion of the object and the amount of light absorbed by the second portion of the object. The default absorption value can be a value in a database associated with the object. The contrast ratio can be a relative difference between the default absorption value and the amount of light absorbed by the object. The characteristic of the object can be a type of the object, a shape of the object, or the material of the object. The characteristic of the object can be indicative of whether the object includes an imperfection or a flaw. The imperfection or the flaw can be an imperfection or a flaw of a weld of part of the object.

When the contrast ratio is above a threshold ratio the object can include the imperfection or the flaw; and when the contrast ratio is below the threshold ratio the object does not include the imperfection or the flaw. The object can include a first portion of the object that is welded to a second portion of the object.

The method can further include applying a light absorbing compound to a surface of the object to increase the contrast ratio. The light absorbing compound can be an infrared (IR) ink. The light absorbing compound can be sprayed onto the surface of the object, painted onto the surface of the compound, or applied as a film on the surface of the object.

According to another aspect of the present disclosure, a method includes: illuminating, by a light source, at least a portion of an object. The object is a material that absorbs or reflects a portion of the light emitted by the light source. The method further includes: measuring, by a sensor, an amount of light absorbed or reflected by the object; determining, by a processing device, a contrast ratio of the absorbed or reflected light by comparing the amount of light absorbed or reflected by the object to a default absorption or reflection value to obtain a difference between the amount of light absorbed or reflected by the object and the default absorption or reflection value; and determining, by the processing device, a characteristic of the object based on the contrast ratio.

The light source can be a laser emitting light at one micron. The light source can include a back plate that reflects light emitted through a bottom of the object.

According to yet another aspect of the present disclosure, a system includes: an object; a light source to transmit light toward the object; a back plate configured to reflect at least a portion of the light emitted from a bottom of the object; a light sensor to measure at least a portion of the light reflected from the joint of the object; and a processing device coupled to the light sensor. The processing device is configured to: determine an amount of light absorbed or reflected by the object; determine a contrast ratio of the absorbed or reflected light by comparing the amount of light absorbed or reflected by the object to a default absorption or reflection value to obtain a difference between the amount of light absorbed or reflected by the object and the default absorption or reflection value; and determine a characteristic of the object based on the contrast ratio.

The contrast ratio can be associated with a portion of the object. The contrast ratio can be associated with an entirety of the object. The object can be a welded object formed from at least two parts joined together by energy directed to the at least two parts, and a wavelength of the energy can be substantially the same as a wavelength of the light transmitted from the light source. The contrast ratio can correspond to a weldability index representative of the absorption properties of the object for weldability. The weldability index can include any subset range falling within a range set of 0-133 out of a scale of 0-255 such that when the weldability index falls within the subset range, the object is deemed to have an acceptable weld quality.

The object can be a welded object formed from at least two parts joined together by energy directed to the at least two parts, and a wavelength of the energy can be substantially the same as a wavelength of the light transmitted from the light source. The contrast ratio can correspond to a weldability index representative of the absorption properties of the object for weldability. The weldability index can include any subset range falling within a range set of 0-133 out of a scale of 0-255 such that when the weldability index falls within the subset range, the object is deemed to have an acceptable weld quality, and when the weldability index falls outside the subset range, the object is deemed to have an unacceptable weld quality.

The object can be a welded object formed from at least two parts joined together by energy directed to the at least two parts, and a wavelength of the energy can be substantially the same as a wavelength of the light transmitted from the light source. The contrast ratio can correspond to a weldability index representative of the absorption properties of the object for weldability. The weldability index can include any subset range falling within a range set of 0-133 out of a scale of 0-255 such that when the weldability index falls within the subset range, the object is deemed to have an acceptable weld quality, and when the weldability index falls outside the subset range, the object is deemed to have an unacceptable weld quality.

BRIEF DESCRIPTION OF THE DRAWINGS

The present description will be understood more fully from the detailed description given below and from the accompanying drawings of various embodiments of the present embodiment, which, however, should not be taken to limit the present embodiment to the specific embodiments, but are for explanation and understanding only.

DETAILED DESCRIPTION OF THE INVENTION

Figure 1:
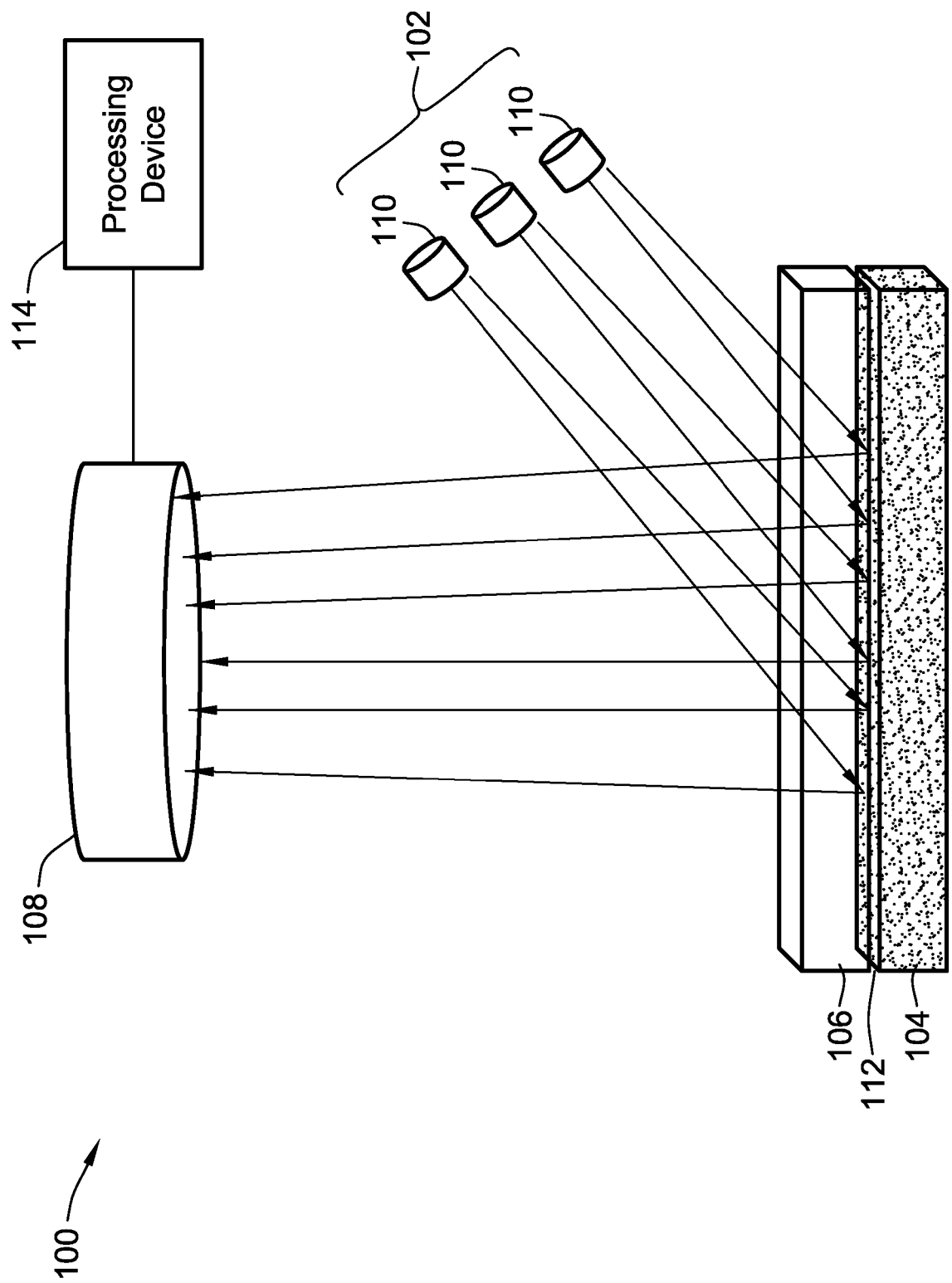
FIG. 1 illustrates an imperfection identification system, according to an embodiment.

The disclosed systems and methods for measuring spectral absorption by objects will become better understood through a review of the following detailed description in conjunction with the figures. The detailed description and figures provide merely examples of the various embodiments described herein. Those skilled in the art will understand that the disclosed examples may be varied, modified, and altered without departing from the scope of the embodiments described herein. Many variations are contemplated for different applications and design considerations; however, for the sake of brevity, each and every contemplated variation is not individually described in the following detailed description.

Throughout the following detailed description, examples of various systems and methods for measuring spectral absorption are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Objects used for various applications may undergo an inspection process prior to being used. For example, objects of an aesthetic nature may be inspected for imperfections to ensure quality control of the objects. Objects that are critical to an operation of a machine may be inspected for imperfections and defects to reduce or eliminate failure of the objects during the operation of the machine. Objects that are joined together by welding or bonding may be inspected to verify the integrity of the weld and the objects after the welding or bonding process.

There are various processes to inspect the objects. In one example, an individual may visually inspect the object to identify surface imperfections in the object. In another example, an optical system may employ a light sensor to capture image data of the object and inspect the object using a software analysis program. An accuracy of the inspection of the object may vary based on environmental conditions. For example, the lighting conditions of the environment where the object is inspected may cause the accuracy of the inspection of the object to vary. When the lighting level is low, imperfections in the object may not be visible. When the light level is bright, imperfections in the object may be washed out by the light.

The radiation pattern of the light may also vary the inspection accuracy of the object. For example, when the light unevenly illuminates surfaces of the object, such as concave or convex surfaces, the imperfections of the object may not be visible or identified. Additionally, as the size and shape of the object varies, the accuracy of the inspection of the object may also vary. The variability of the accuracy of the inspection of the objects may lead to increased imperfections and failures of objects that were approved during inspections.

The embodiments described herein may address the above-noted deficiencies by providing systems and methods for measuring spectral absorption of an object for detection of imperfections. The systems and methods for measuring spectral absorption of an object may include a light guide to direct light from a light source and illuminate an object with light at a desired level. In one example, the light guide may diffuse or disperse light from a light source to evenly illuminate the object or a portion of the object. In another example, the light guide may focus the light from the light source to illuminate a portion of the object. The light guide may increase the accuracy of the object inspection by reducing or eliminating variations in the environment and/or variations in the inspection caused by varying sizes or shapes of the objects. The systems and methods for measuring spectral absorption of an object may also include a light sensor for measuring an absorption and/or reflection of the light from the object. The systems and methods for measuring spectral absorption of an object may also include a processing device to determine a gradient pixel value of the reflected or absorbed light and identify whether the object includes imperfections.

FIG. 1 illustrates an imperfection identification system 100, according to an embodiment. The imperfection identification system 100 may be configured to determine the light characteristics of an object to identify imperfections in an object 106. The light characteristics may include light absorption properties of the object 106. In one embodiment, the object 106 may include one or more polymers that absorb various wavelengths of light. In one example, the imperfection identification system 100 may be used by a resin supplier to measure the light characteristics of the object 106 that includes resin material to identify imperfections in the object 106. The imperfection identification system 100 may be used to identify an imperfection in a single object 106 or in a batch or group of objects 106. In one example, the object 106 may be custom or unique compounded polymers used for injection molding and/or sample couponing, and the imperfection identification system 100 may be used to identify imperfections or abnormalities in the custom or unique compounded polymers.

The imperfection identification system 100 may include a light source 102, a back plate 104, an object 106, and a light sensor 108. The light source 102 may include one or more lighting elements 110. In one example, the lighting elements 110 may be incandescent light bulbs, halogen light bulbs, full-spectrum light sources, or fluorescent light bulbs. In another embodiment, the lighting elements 110 may be light emitting diodes (LEDs), halogen lights, ultraviolet lights, compact fluorescent lamps (CFLs), a laser, infrared lights, and so forth. The lighting elements 110 may radiate light at a defined wavelength or wavelength spectrum. In one embodiment, the light may be a low band ultraviolet light or a high band ultraviolet light with a wavelength spectrum ranging between 350 nanometers (nm) and 450 nm. In another embodiment, the light may be near-infrared light with a wavelength spectrum ranging between 750 nm and 1100 nm. In another embodiment, the light may be laser light of one micron, such as ranging between 950 nm and 1100 nm. In another embodiment, the light may be infrared light with a wavelength spectrum ranging between 1700 nm and 2000 nm. In another embodiment, the light may be a single wavelength of light, such as 1550 nm that is the wavelength of light absorbed by water. When the imperfection or defect sought to be identified through non-destructive means is a weld joint or welded area, the wavelength of the infrared light can be chosen to be the same or substantially the same as the wavelength of the energy used to create the weld. For example, when one part is clear (transmissive to laser) and the other part is opaque (absorbing laser), and they are welded together using a 960 nm laser (also called a 1 μm laser), then the infrared wavelength is selected to be 960 nm or substantially the same as 960 nm (e.g., within 1% or 5% or 10% of 960 nm). Matching the wavelength of the energy used to make the weld with the light energy (e.g., infrared) used to illuminate the weld is a non-destructive way of visualizing the quality of the weld by assessing, for example, the pixel values of the weld from the absorbed light. No cutting of the parts are required to check their weldability.

In one embodiment, the light source 102 may illuminate the object 106 for inspection. In one example, the object 106 may be an object from a resin supplier, where the object 106 is part of a master batch of laser-absorbing objects used to gauge a level of laser absorption and/or transmissivity by the object 106. As discussed below, the imperfection identification system 100 may be used for inspecting object 106, prior to the object 106 is welded (also referred to as pre-weld) or after the object 106 is welded (also referred to as post-weld) for absorption and/or transmissivity of the object 106. For example, a pre-welded object 106 may be inspected to determine the viability of the object 106 for laser plastic welding. In one embodiment, the imperfection identification system 100 may inspect a complete assembly of parts of the object 106 for laser welding. In another embodiment, the imperfection identification system 100 may inspect an individual part or portion of the object 106. In another embodiment, the imperfection identification system 100 may inspect a sample number of transmissive objects 106 in a master batch. In another embodiment, the imperfection identification system 100 may inspect a pre-compounded polymer or stock polymer of the object 106. In another embodiment, the imperfection identification system 100 may inspect a doped object 106. As discussed below, the doped object 106 may be a polymer object doped with a compound, such as a glass fill, a fiber fill, a colorant compound, an absorber compound, a soot compound, and so forth.

The light may emit light towards the back plate 104 and/or the object 106. In one example, the back plate 104 and/or the object 106 may reflect at least a portion of the light. In another example, the back plate 104 and/or the object 106 may absorb at least a portion of the light. In one example, the back plate 104 may be a light table. In another example, when the back plate 104 reflects lights, the back plate 104 may be a white plastic material. In another example, when the back plate 104 absorbs lights, the back plate 104 may be a black plastic material. In another example, the back plate 104 may be different colors and/or materials to adjust a reflective nature and/or absorptive nature of the back plate 104 to provide a desired light reflection or light absorption characteristic.

In one embodiment, the object 106 may be transmissive material. In another example, the object 106 may be absorptive material. In one example, the back plate 104 may be reflective material that reflects light and the object 106 may be transmissive material. In another embodiment, the object 106 may be a clear material, a partially clear material, a visibly opaque material, or a visibly colored material.

In one embodiment, the back plate 104 may be separate from the object 106. In one example, the back plate 104 may abut the object 106. In another example, the back plate 104 may be separated from the object 106 by a gap. In another embodiment, the back plate 104 may be joined to the object 106 by a joint 112. For example, the back plate 104 may be joined to the object 106 by laser welding, ultrasonic welding, gluing, solvent bonding, hot plate welding, infrared welding, and so forth. For example, laser welding may use a laser beam to provide a concentrated heat source to form narrow, deep welds and high welding rates between the back plate 104 and the object 106. The laser welding may be used in high volume applications using automation, such as in the automotive industry.

For example, the joint 112 or the back plate 104 or the object 106 may reflect at least a portion of the light from the light source 102 toward the light sensor 108. The light sensor 108 may measure the amount of light reflected by the joint 112, the back plate 104, or the object 106. In one example, the light sensor 108 may be a full spectrum light sensor that may measure light reflected across a full light spectrum. In another example, the light sensor 108 may measure a portion of light reflected within a light spectrum range. In another example, the light sensor 108 may be a still-image camera, a video camera, an infrared sensor, and so forth.

The light sensor 108 may be coupled to a processing device 114. The light sensor 108 may send light measurement information to the processing device 114. The processing device 114 may analyze the light measurement information to determine whether there may be any imperfections or defects in the joint 112, the back plate 104, or the object 106 of the object 106. In one example, when the processing device 114 detects an imperfection or a defect in the object 106, the processing device 114 may send an alert notification to a user, such as by displaying an alert on a display or user interface or communicating the notification to another device. In another example, when the processing device 114 does not detect an imperfection or a defect in the object 106, the processing device 114 may send an approval notification to a user, such as by displaying a message on a display or user interface or communicating the notification to another device.

In one example, the processing device 114 may compare the light measurements with a predefined measurement to determine if the amount of light absorbed by the object 106 is within an acceptable range that indicates there are not imperfections or defects. When the amount of light absorbed by the object 106 is within an acceptable range, the processing device 114 may send the approval notification. When the amount of light absorbed by the object 106 is not within the acceptable range, the processing device 114 may send the error notification. In another example, the processing device 114 may compare different portions of the joint 112, the back plate 104, and/or the object 106 to determine a contrast level between the different portions. When the contrast level is within an acceptable range, the processing device 114 may send the approval notification. When the contrast level is not within the acceptable range, the processing device 114 may send the error notification.

In one example, the imperfection identification system 100 may be used to inspect polymer objects for light absorption characteristics and/or light transmissivity characteristics that include a weld and/or polymer objects that have not been welded together. The object may be a complete assembly of parts for laser welding (welded or not welded), individual parts of the object 106, material sample chips or master batches, pre-compounded polymer or stock polymer, polymers doped with any compound, such as a glass/fiber fills, colorants, absorbers, soot, etc.

Figure 2:
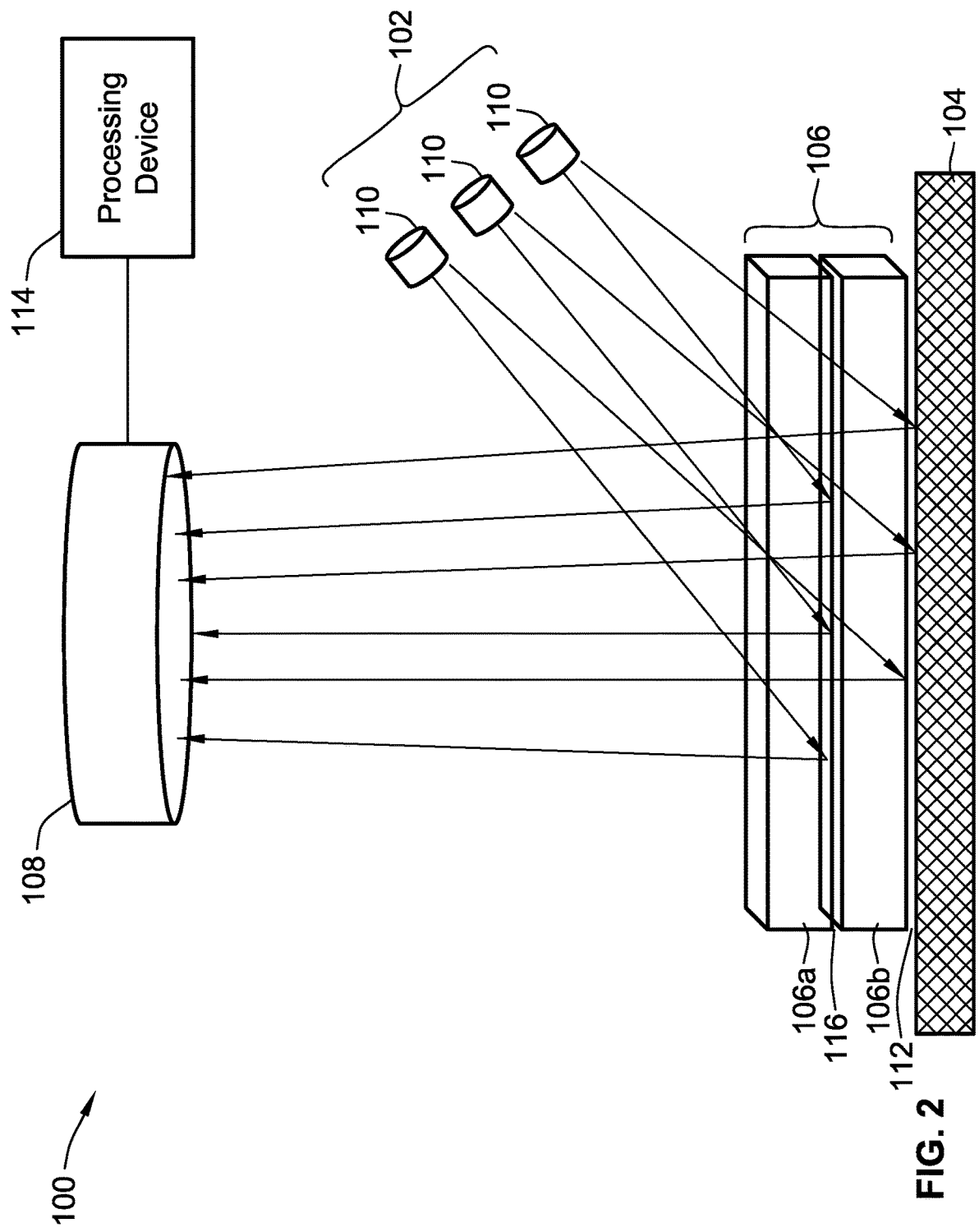
FIG. 2 illustrates the imperfection identification system in FIG. 1 with the object including multiple transmissive parts, according to an embodiment.

FIG. 2 illustrates the imperfection identification system 100 in FIG. 1 with the object 106 including multiple transmissive parts, according to an embodiment. Some of the features in FIG. 2 are the same or similar to some of the features in FIG. 1 as noted by same reference numbers, unless expressly described otherwise. In one embodiment, the object 106 may include a first portion 106*a* and a second portion 106*bb*.

In one example, the first portion 106*a* and/or the second portion 106*b* may reflect at least a portion of the light. In another example, the first portion 106*a* and/or the second portion 106*b* may absorb at least a portion of the light. In one embodiment, the first portion 106*a* and/or the second portion 106*b* may be transmissive material. In another embodiment, the first portion 106*a* and/or the second portion 106*b* may be absorptive material. In one example, the first portion 106*a* may be transmissive material and the second portion 106*b* may be transmissive material. In another example, the first portion 106*a* may include transmissive material and the second portion 106*b* may be absorptive material. In another example, the first portion 106*a* may include absorptive material and the second portion 106*b* may be transmissive material. In another example, the first portion 106*a* may include absorptive material and the second portion 106*b* may be absorptive material.

In one embodiment, the first portion 106*a* may be joined to the second portion 106*b*. For example, the first portion 106*a* may be joined to the second portion 106*b* by laser welding, ultrasonic welding, gluing, solvent bonding, hot plate welding, infrared welding, and so forth. For example, laser welding may use a laser beam to provide a concentrated heat source to form narrow, deep welds and high welding rates between the first portion 106*a* and the second portion 106*b*. The laser welding may be used in high volume applications using automation, such as in the automotive industry.

The joining technique may form a joint 116 where the first portion 106*a* and the second portion 106*b* are joined together. In one example, the light source 102 may illuminate the joint 116 for inspection. In another example, the light source 102 may illuminate at least a portion of the first portion 106*a* and/or the second portion 106*b* for inspection.

For example, the joint 116, the first portion 106*a*, the second portion 106*b*, the joint 112, and/or the back plate 104 may reflect at least a portion of the light from the light source 102 toward the light sensor 108. The light sensor 108 may be coupled to a processing device 114. As discussed above, the light sensor 108 may send light measurement information to the processing device 114. The processing device 114 may analyze the light measurement information to determine whether there may be any imperfections or defects in the joint 116, the first portion 106*a*, or the second portion 106*b* of the object 106. In one example, when the processing device 114 detects an imperfection or a defect in the object 106, the processing device 114 may send an alert notification to a user, such as by displaying an alert on a display or user interface or communicating the notification to another device. In another example, when the processing device 114 does not detect an imperfection or a defect in the object 106, the processing device 114 may send an approval notification to a user, such as by displaying a message on a display or user interface or communicating the notification to another device.

In one example, the processing device 114 may compare the light measurements with a predefined measurement to determine if the amount of light reflected by the object 106 is within an acceptable range that indicates there are not imperfections or defects. When the light measurements are within an acceptable range, the processing device 114 may send the approval notification. When the light measurements are not within the acceptable range, the processing device 114 may send the error notification. In another example, the processing device 114 may compare different portions of the joint 116, the first portion 106a, and/or the second portion 106b to determine a contrast level between the different portions. When the contrast level is within an acceptable range, the processing device 114 may send the approval notification. When the contrast level is not within the acceptable range, the processing device 114 may send the error notification. When the imperfection or defect is a defect in a weld joining two parts together, the contrast level can correspond to a weldability index, which is a value, such as a pixel value, representative of the infrared absorption properties of the parts for weldability. The weldability index, in some embodiments, can be in a range of 0-133 out of a scale of 0-255 (grayscale), or any range in between 0-133. Parts having a weldability index outside of the range, such as between 134-255, can be deemed as not falling within the acceptable range, and the processing device 114 can send the error notification.

Figure 3:
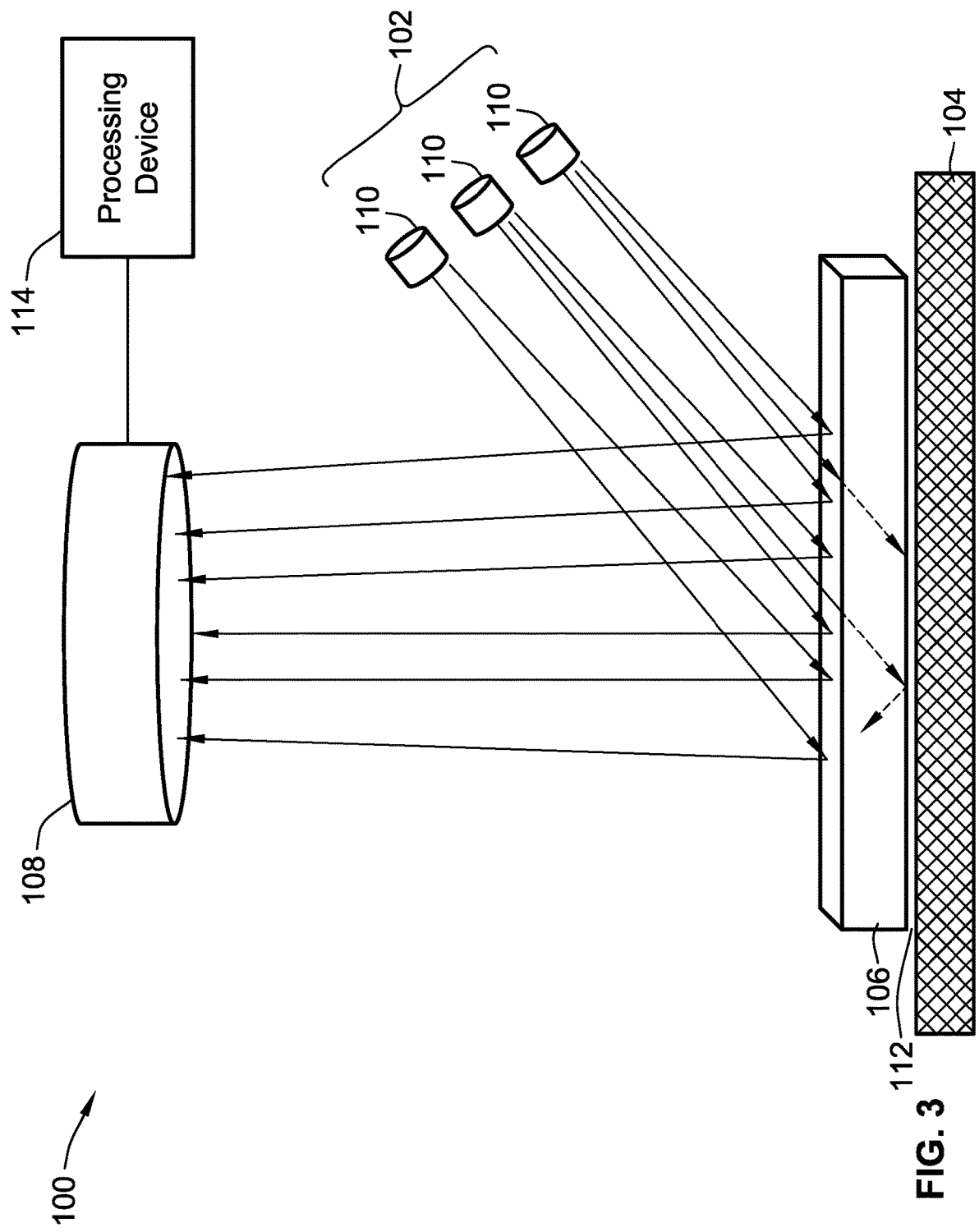
FIG. 3 illustrates the imperfection identification system in FIG. 1 with the object including a light absorbing material, according to an embodiment.

FIG. 3 illustrates the imperfection identification system 100 in FIG. 1 with the object 106 including light absorbing material, according to an embodiment. Some of the features in FIG. 3 are the same or similar to some of the features in FIGS. 1-2 as noted by same reference numbers, unless expressly described otherwise. In one embodiment, the object 106 may be a light absorbing material that may absorb a first portion of the light from the light source 102 and may reflect a second portion of the light from the light source 102. In one example, a first portion of the light waves from the light source 102 may only travel through a portion of the object 106 before being absorbed and a second portion of the light waves from the light source 102 may only travel through a portion of the object 106 before being reflected. In this example, the light waves may not reach the back plate 104 such that all the light waves received by the light sensor 108 are reflected directly by the object 106. In another example, a first portion of the light waves from the light source 102 may travel through the object 106 before being absorbed or reflected by the back plate 104, a second portion of the light waves from the light source 102 may only travel through a portion of the object 106 before being absorbed, and a third portion of the light waves from the light source 102 may only travel through a portion of the object 106 before being reflected. In this example, the light waves received by the light sensor 108 are reflected directly by the object 106.

Figure 4:
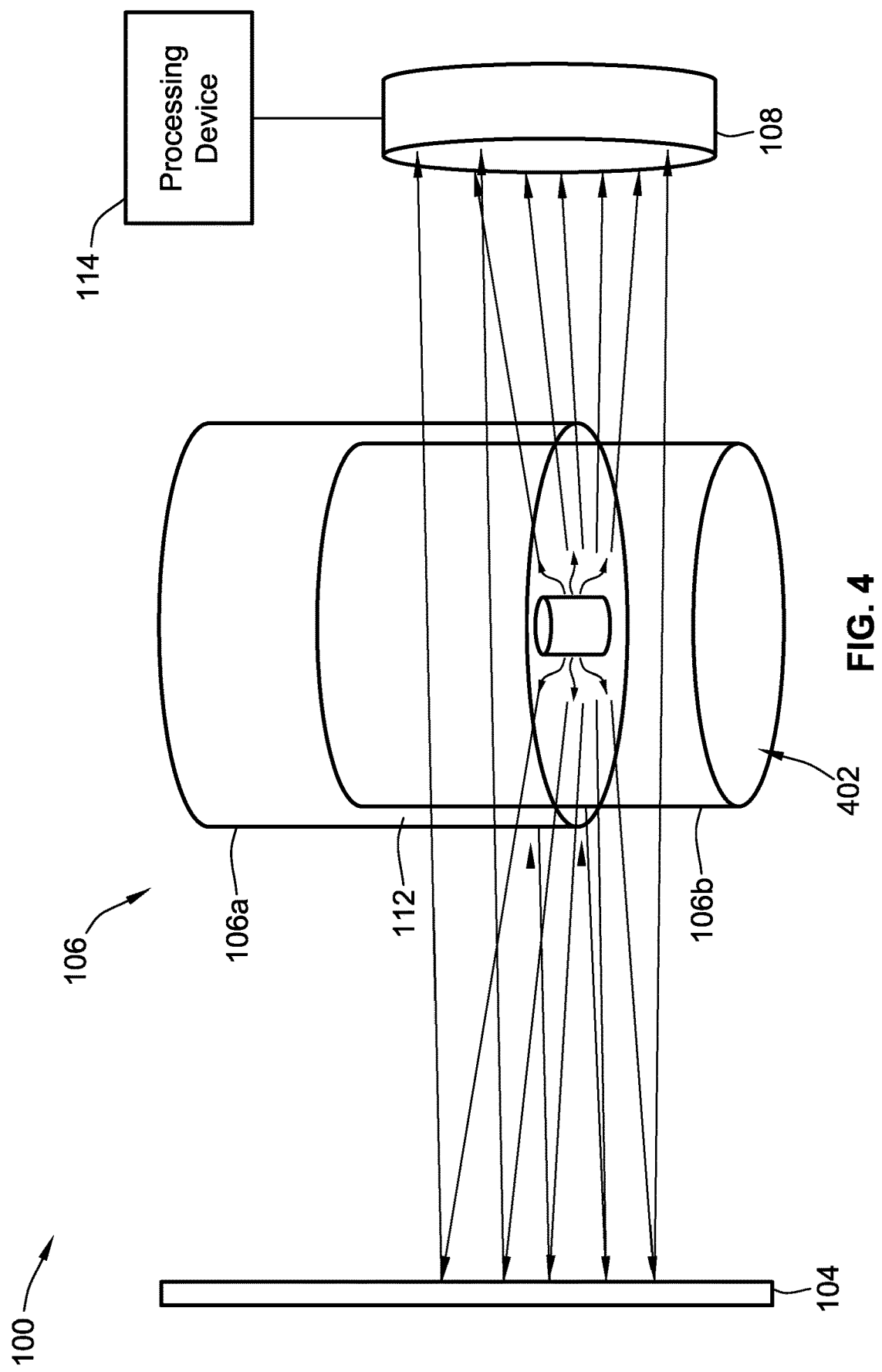
FIG. 4 illustrates the imperfection identification system in FIG. 1 with the light source located within the object and a back plate to reflect and/or absorb light transmitted through the object, according to an embodiment.

FIG. 4 illustrates the imperfection identification system 100 in FIG. 1 with the light source 102 located within the object 106 and a back plate 104 to reflect and/or absorb light transmitted through the object 106, according to an embodiment. Some of the features in FIG. 4 are the same or similar to some of the features in FIGS. 1-3 as noted by same reference numbers, unless expressly described otherwise.

The object 106 may include a cavity 402. The cavity 402 may be an empty space within the object 106. The light source 102 may be shaped to fit within the cavity 402. In one example, the light source 102 may be located approximate the joint 112 or approximate a surface of the object 106.

In one embodiment, when the light source 102 is located within the cavity of the object 106, the light source 102 may diffuse or focus the light from the light source 102 onto a portion of the back plate 104, the object 106, and/or the joint 112 of the object 106. In another embodiment, when the light source 102 is located within the cavity 402 of the object 106, the light may diffuse from the light source 102 to substantially illuminate the entire object 106. In one example, the object 106 may be cylinder shaped, square shaped, rectangular shaped, or another shape. In another example, the object 106 may include a first portion 106a and a second portion 106b. In one embodiment, the first portion 106a may be inserted or fit within the second portion 106b. In another embodiment, the first portion 106a may be attached or welded to the second portion 106b. The light sensor 108 may measure an amount of light transmitted through the object 106 for analysis by the processing device 114.

In one embodiment, when the light source is located within the cavity 402, the light sensor 108 and processing device 114 of the imperfection identification system 100 may be configured to detect a circumferential weld. For example, as the light sensor 108 and/or the back plate 104 illuminates the object 106 the light sensor 108 and the processing device 114 may capture a circumferential image of the object 106. In one example, the object 106 may rotate about an axis such that the light sensor 108 may capture a circumferential image of the object 106. In another example, the light sensor 108 may rotate about an axis such that the light sensor 108 may capture a circumferential image of the object 106. In one embodiment, the circumferential image may be a continuous image of the object 106. In another embodiment, the circumferential image may include multiple images that the processing device 114 may stitch, aggregate, or combine together to generate a full view of the circumferential weld. The processing device 114 may analyze the circumferential image to identify an abnormality or imperfection in the circumferential weld.

Figure 5:
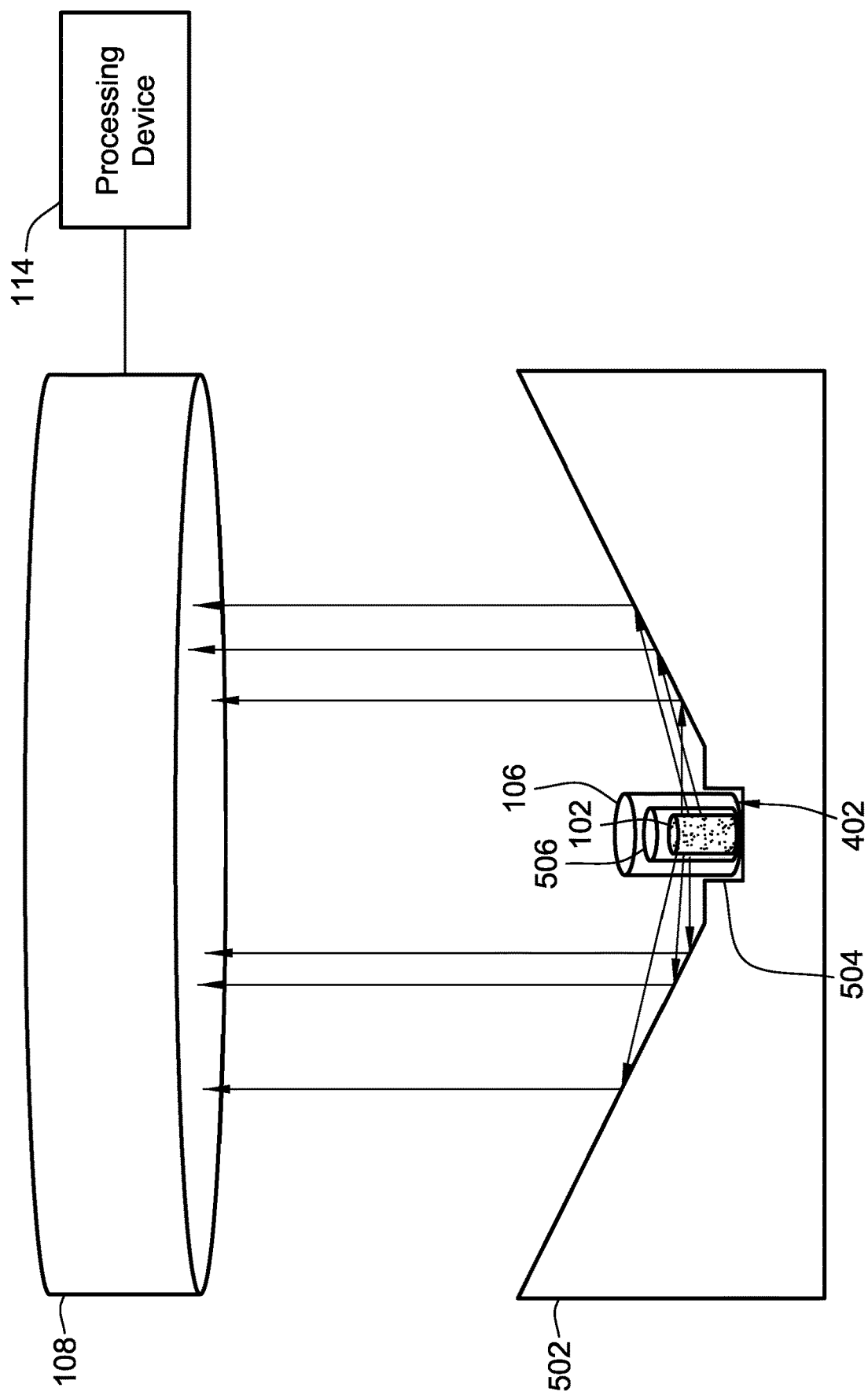
FIG. 5 illustrates the imperfection identification system in FIG. 1 with a conical mirror, according to an embodiment.

FIG. 5 illustrates the imperfection identification system 100 in FIG. 1 with a conical mirror 502, according to an embodiment. Some of the features in FIG. 5 are the same or similar to some of the features in FIGS. 1-4 as noted by same reference numbers, unless expressly described otherwise.

The imperfection identification system 100 may include the light source 102 and a light guide 506 located within the cavity 402 of the object 106, as in FIG. 4. The light guide 506 may direct light from the light source 102 and illuminate the object 106 with light at a desired level. In one example, the light guide 506 may diffuse or disperse light from the light source 102 to evenly illuminate the object 106 or a portion of the object 106. In another example, the light guide 506 may focus the light from the light source 102 to illuminate a portion of the object 106.

The light guide 506 may increase the accuracy of the object inspection by reducing or eliminating variations in the environment and/or variations in the inspection caused by varying sizes or shapes of the objects 106.

In one embodiment, the light source 102, the light guide 506, and the object 106 may be located within a cavity 504 of the conical mirror 502. The cavity 504 may be an indent, groove, or depression in the conical mirror 502. In one example, the cavity 504 may be located at a center of the middle of the conical mirror 502. In one example, the conical mirror 502 may be a cone-shaped concave mirror. As light is emitted from the object 106 through the light guide 216 and the object 106, the conical mirror 502 may reflect the light toward the light sensor 108. The conical mirror 502 may reflect the light to increase an amount of light received at the light sensor 108. The increased amount of light received at the light sensor 108 may increase an accuracy of the light measurements used by the processing device 114 to detect imperfections and defects in the object 106.

Figure 6:
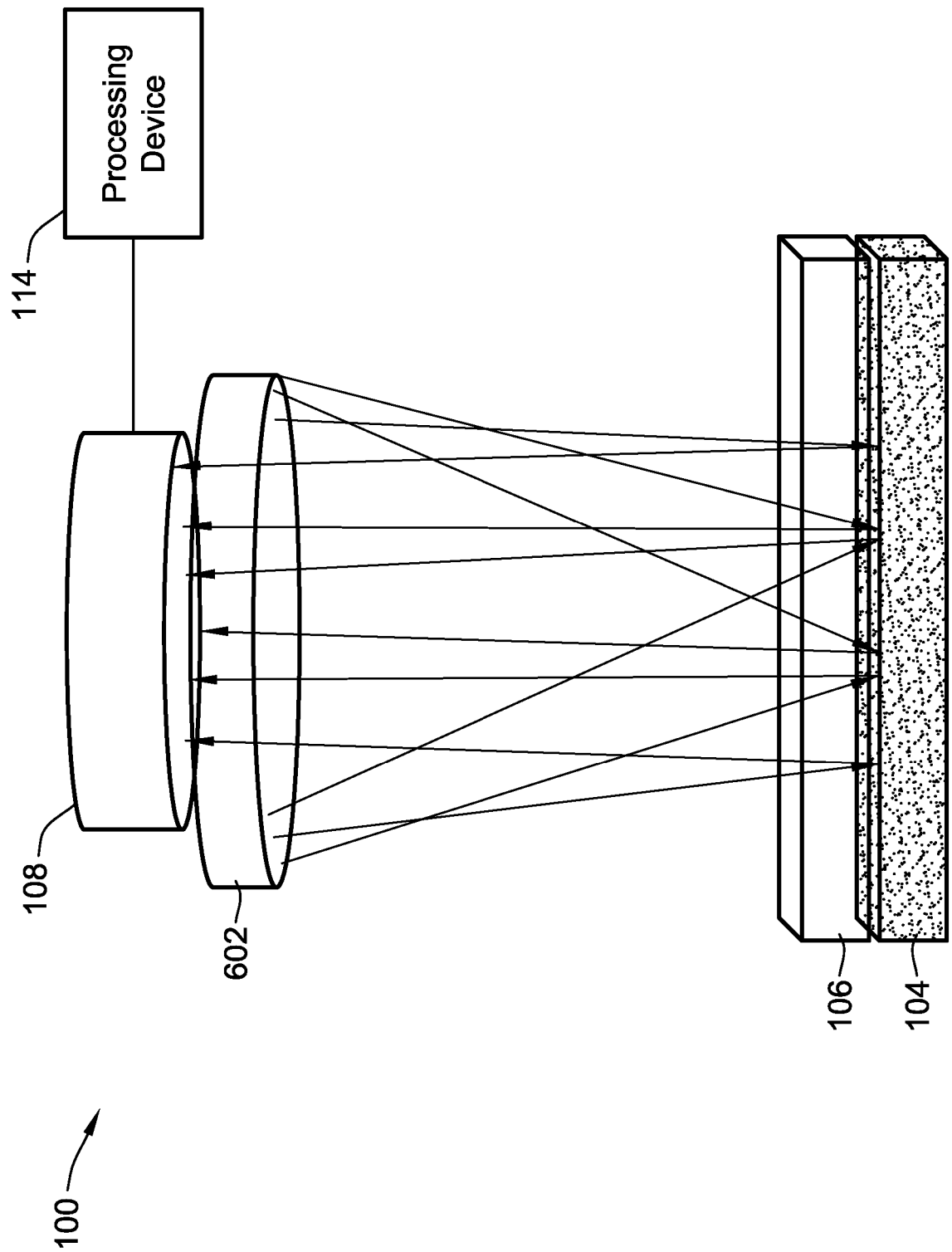
FIG. 6 illustrates the imperfection identification system in FIG. 1 with a light source mounted to the light sensor, according to an embodiment.

FIG. 6 illustrates the imperfection identification system 100 in FIG. 1 with a light source 602 mounted to the light sensor 108, according to an embodiment. Some of the features in FIG. 6 are the same or similar to some of the features in FIGS. 1-5 as noted by same reference numbers, unless expressly described otherwise. The light source 602 may have the same characteristics as the light source 102 discussed above. The light source 602 may be mounted to the light sensor 108. In one embodiment, the light source 602 may be attached to the light sensor 108. In another embodiment, the light source 602 may be located approximate and below the light sensor 108. For example, the light source 602 may be a ring light that includes a single circular light source or multiple light sources in a circular pattern. The light sensor 108 may be located within the middle or center of the ring light. The light source 602 may diffuse the light onto the object 106 to eliminate shadows of the object 106. The light sensor 108 may then detect light absorbed by the object 106 to identify an imperfection or abnormality in the object 106.

Figure 7:
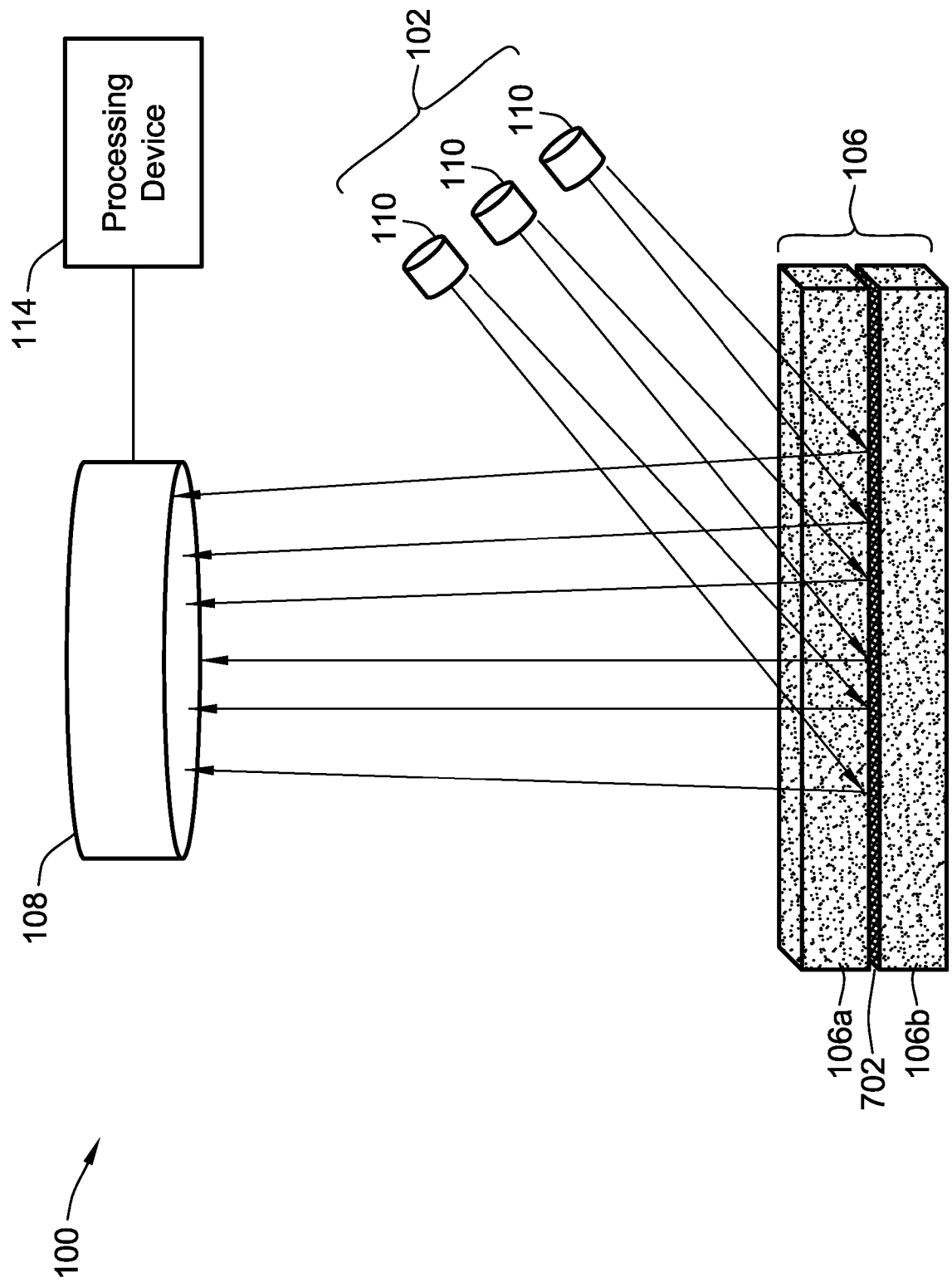
FIG. 7 illustrates the imperfection identification system in FIG. 1 with the object that includes a light absorbing compound between the first portion of the object and the second portion of the object, according to an embodiment.

FIG. 7 illustrates the imperfection identification system 100 in FIG. 1 with the object 106 that includes a light absorbing compound 702 between the first portion 106a of the object 106 and the second portion 106b of the object 106, according to an embodiment. Some of the features in FIG. 7 are the same or similar to some of the features in FIGS. 1-6 as noted by same reference numbers, unless expressly described otherwise.

In one embodiment, the light absorbing compound 702 may be applied to a surface of the object 106. In one example, when the object 106 includes the first portion 106a and the second portion 106b, the light absorbing compound 702 may be applied between the first portion 106a and the second portion 106b. The light absorbing compound 702 may be an infrared (IR) ink or IR paint. In one example, the light absorbing compound 702 may absorb a greater amount of light than the material of the first portion 106a and/or second portion 106b of the object 106 to increase a contrast ratio between any imperfections or abnormalities of the object 106 and the rest of the material or welds of the object 106. The light absorbing compound 702 may be applied to the first portion 106a and/or the second portion 106b of the object 106 via being sprayed on, painted on, with a film, and so forth. In one example, when the contrast ratio between the imperfections or abnormalities of the object 106 and the rest of the material or welds of the object 106 is increased, the processing device 114 may more accurately identify the imperfections or abnormalities when comparing the imperfections or abnormalities to a library or database of normal images of the material and/or welds, as discussed below.

In another example, the processing device 114 may analyze the light reflected by the light absorbing compound 702 to determine whether the light absorbing compound 702 was properly applied to the object 106. When a first area or portion of the object 106 where the light absorbing compound 702 has a first absorption level and a second area or portion of the object 106 where the light absorbing compound 702 has a second absorption level that is different than the first absorption level, the processing device 114 may determine that the light absorbing compound 702 was not evenly or properly applied.

Figure 8:
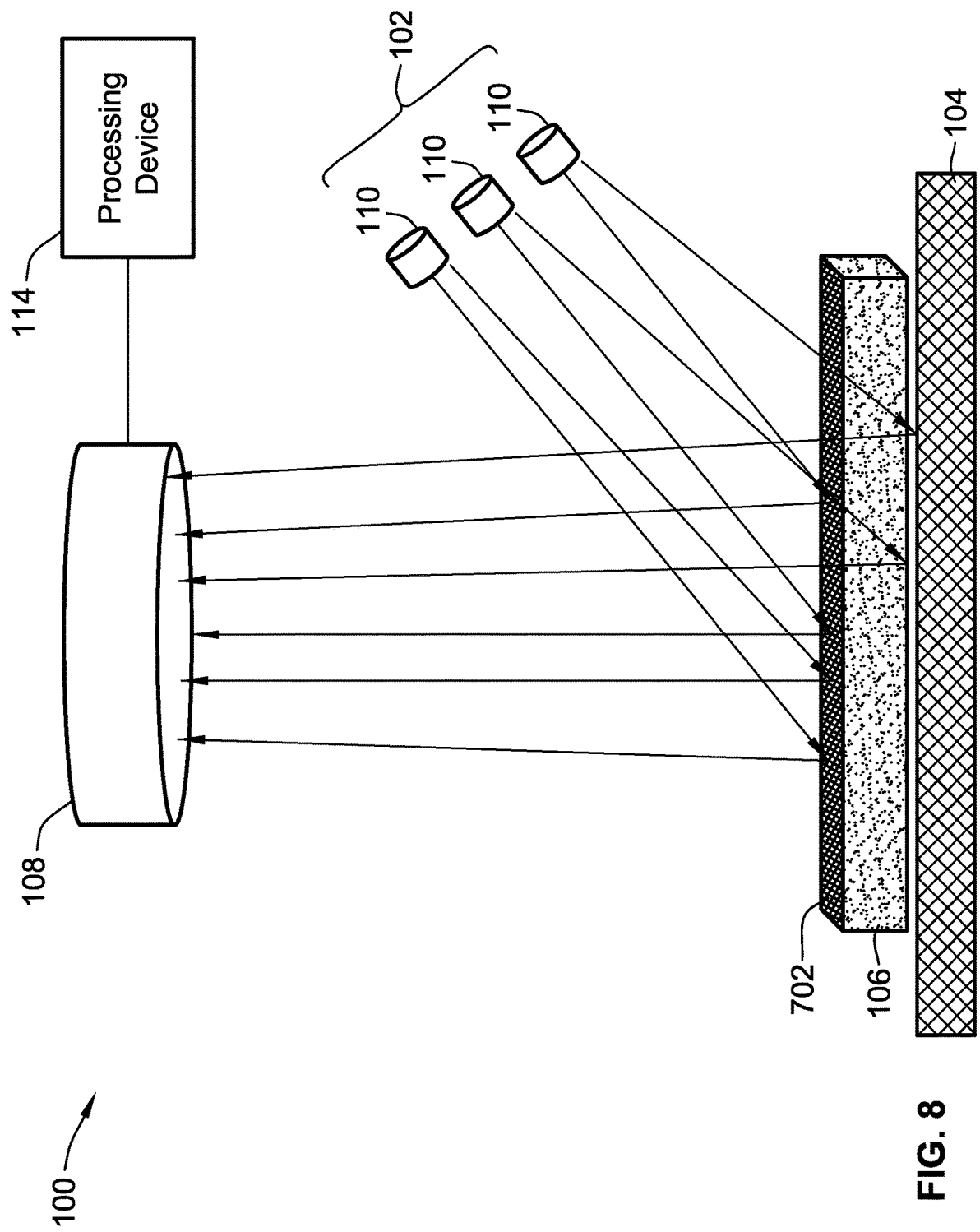
FIG. 8 illustrates the imperfection identification system in FIG. 1 with a top surface of the object including a light absorbing compound, according to an embodiment.

FIG. 8 illustrates the imperfection identification system 100 in FIG. 1 with a top surface of the object 106 including a light absorbing compound 702, according to an embodiment. Some of the features in FIG. 8 are the same or similar to some of the features in FIGS. 1-7 as noted by same reference numbers, unless expressly described otherwise. As discussed above, the light absorbing compound 702 may be applied it any surface of the object 106. When the object 106 is a single material or a unified object, the light absorbing compound 702 may be applied to a surface of the object 106, such as a top or bottom surface. When the light absorbing compound 702 is applied to the surface of the object 106, the contrast ratio between the imperfections or abnormalities of the surface of the object 106 and the normal material or welds of the object 106 may be increased to increase an accuracy of the processing device 114 identifying the imperfections or abnormalities.

Figure 9:
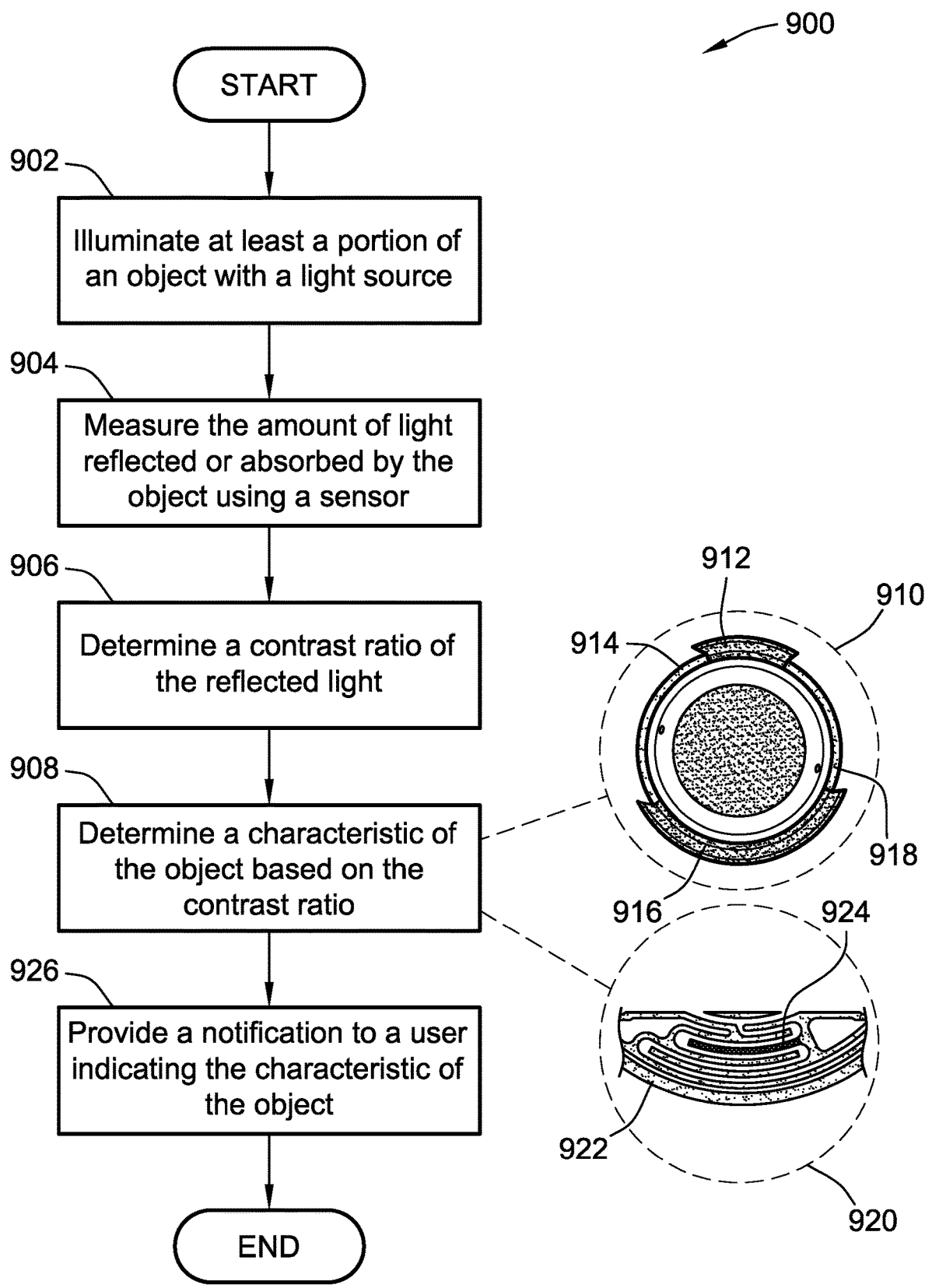
FIG. 9 illustrates a flowchart of a method to identify an imperfection in the object, according to an embodiment.

FIG. 9 illustrates a flowchart 900 of a method to identify an imperfection in the object 106, according to an embodiment. Some of the features in FIG. 9 are the same or similar to some of the features in FIGS. 1-8 as noted by same reference numbers, unless expressly described otherwise. The method may include illuminating at least a portion of an object with a light source (block 902). In one embodiment, as the object is illuminated, the object may absorb or reflect light from the light source. In one example, when the object is void of flaws or imperfections, the entire object may absorb the light at approximately the same absorption level. In another example, when the object is void of flaws or imperfections, the entire object may reflect the light at approximately the same reflection level. In another example, a first portion of the object may absorb or reflect light at a first level and a second portion of the object may absorb or reflect light at a second level. In one example, when the object includes a weld that connects or fuses two objects into a single object, the first portion of the object may be the material that is not welded that may absorb or reflect light at a first level and the second portion of the object may be where the objects are welded together and the weld may absorb or reflect the light at a second level. The weld can be formed by directing energy, such as laser energy, to the two parts that form the object. The wavelength of that energy can be substantially the same (e.g., within 1-15% of each other) as the wavelength of the light from the light source. It has been found that when the wavelengths are matched, the quality of the weld can be reliably and objectively determined by a machine without subjective human interpretation.

In another example, when the object includes flaws or imperfections, the first portion of the object may be a part of the object that does not include the flaw or imperfection and the second portion of the object may be a part of the object with the flaw or imperfection. In this example, the flaw or imperfection may absorb or reflect light at a different level than the part of the object without the flaw or imperfection. In another example, the first portion and the second portion of the object may be different parts of the weld. When the weld is a good weld without flaws, imperfections, or weaknesses in the weld, the light may be absorbed or reflected by the first portion and the second portion of the object at the same level. When the weld is a bad weld that includes flaws, imperfections, or weaknesses in the weld, the light may be absorbed or reflected by the first portion and the second portion of the object at different levels. As described above, the quality of the weld can be characterized as a weldability index. The weldability index, in some embodiments, can be in a range of 0-133 out of a scale of 0-255 (e.g., grayscale), or any subset range from 0-133, e.g., 0-125, or 0-130, and so on. The precise threshold for good/bad weldability quality can be based on external requirements that the skilled person will appreciate, such as the type of object being welded, its application, customer requirements, and the like. This threshold can be easily changed by an operator of the illumination device based on the application or customer's requirements.

The method may include measuring, by a sensor, an amount of light that is reflected by the object. (Block 904). In one example, the sensor may be an optical sensor that may measure an amount of light that is reflected by the object. The amount of light reflected may be the amount of light not absorbed by the object. In another example, the sensor may be an optical sensor that may measure an amount of light that is absorbed by the object. The amount of light absorbed may be the amount of light not reflected by the object. The method may include determining a gradient pixel value or contrast ratio of the reflected light for at least a portion of the object. (Block 906). In one example, a processing device may receive an image from the sensor indicative of the amounts of light reflected or absorbed by the object at different locations on the object. The processing device may compare the amount of light reflected between the different locations on the object to determine a contrast ratio (or weldability index) between the different locations. In one embodiment, the processing device may determine the absolute value of the difference between the reflection levels at the two locations to determine the contrast ratio (or weldability index). In another embodiment, the processing device may determine a relative difference between the reflection levels at the two locations to determine the contrast ratio (or weldability index).

In another embodiment, the processing device may access or store a database of desired or default reflection or absorptions levels for an object or a part of an object. In one example, the database may include multiple reflection level values and/or absorption level values for different default characteristics of the object, such as different type of object, different shapes of objects, different materials for objects, different locations along the object, and so forth. In one example, the sensor may detect the default characteristics of the object using sensor measurements by the sensor. For example, the sensor may be an optical sensor that may determine a color of the object to select the default characteristics of the object. In another example, the sensor may measure dimensional information of the object to select the default characteristics of the object. In another example, the processing device may receive the default characteristics from an input device, such as a touch screen, a keyboard, a mouse, and so forth. In another example, the default characteristic may be a measurement taken without an object located below the light source, such that the light reflects off of a back plate and directly to the sensor. The processing device may determine the contrast ratio by determining a difference between a desired reflection level or desired absorption level in the database with the measured reflection level or measure absorption level by the sensor.

In one embodiment, the method may include determining a characteristic of the object based on the contrast ratio. (Block 908). In one example, the characteristic of the object may be an imperfection of the object, a flaw of the object, a homogeneity level of the object, a strength level of a weld of the object, a weakness level of the weld of the object, a welding characteristic of the object (such as whether the material of the object is weldable), and so forth. In another example, the characteristic of the object may include material that transitions from transmissive material to absorptive material, material that transitions from transmissive material to transmissive material, material that transitions from transmissive material to transmissive material with an additional applied or doped absorber, a single transmissive object, a single absorptive object, light absorbing compounds applied to the object, material with compounds doped into the material, object joint types (such as ultrasonic welds, gluing, solvent bonds, hot plate welds, IR welds), and so forth.

The characteristic of the object may be indicative of the determined contrast ratio (or weldability index). For example, when the determined contrast ratio is below a threshold amount or threshold ratio, the contrast ratio may indicate that the object does not have an imperfection. In another example, when the determined contrast ratio is above a threshold amount, the contrast ratio may indicate that the object includes an imperfection. Alternately, when the weldability index is below a threshold value, the weldability index can indicate that the object does have an imperfection, as explained above. In another example, when the weldability index is above a threshold value, the weldability index can indicate that the object does not have any unacceptable imperfection.

In one example, object 910 includes a first portion 912 with a first contrast ratio, a second portion 914 with a second contrast ratio, a third portion 916 with a third contrast ratio, and a fourth portion 918 with a fourth contrast ratio. The first contrast ratio of the first portion 912 and the third contrast ratio of the third portion 916 may be below the threshold amount, indicating that the first portion 912 and the third portion 916 of the object do not have imperfections. The second contrast ratio of the second portion 914 and the fourth contrast ratio of the fourth portion 918 may exceed the threshold amount, indicating that the second portion 914 and the fourth portion 918 of the object include imperfections.

In another example, object 920 includes a first portion 922 with a first contrast ratio and a second portion 924 with a second contrast ratio. The first contrast ratio of the first portion 922 may be below the threshold amount, indicating that the first portion 922 may have a weld with a strength level above a threshold level. The second contrast ratio of the second portion 924 may exceed the threshold amount, indicating that the second portion 924 may have a weld with a weakness level above a threshold level. The method may include providing a notification to a user indicating a characteristic of an object, such as whether the object includes an imperfection, a flaw, a strong weld, a weak weld, and so forth. (Block 926). The notification may include a message displayed on a display, a text message, highlighting a portion of an image of the object, and so forth.

The disclosure above encompasses multiple distinct embodiments with independent utility. While each of these embodiments has been disclosed in a particular form, the specific embodiments disclosed and illustrated above are not to be considered in a limiting sense as numerous variations are possible. The subject matter of the embodiments includes all novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

What is claimed is:

1. A method, comprising:
    illuminating, by a light source, an entire object, wherein:
        the light source is a laser emitting light having a wavelength of about one micron;
        the light source includes a back plate that reflects light emitted through a bottom of the object;
        the object is a material that absorbs a portion of the light emitted by the laser;
    measuring, by a sensor, an amount of light absorbed by a first portion of the object, wherein the amount of light absorbed by the object is the amount of light not reflected by the object;
    determining, by a processing device, a contrast ratio of the absorbed light by comparing the amount of light absorbed by the object to a default absorption value that is indative of an amount of light absorbed by a second portion of the object, wherein the contrast ratio is a difference between the amount of light absorbed by the first portion of the object and the amount of light absorbed by the second portion of the object;
    determining, by the processing device, a characteristic of the object based on the contrast ratio; and
    providing a notification to a user indicating the characteristic of the object.

2. The method of claim 1, wherein the default absorption value is a value in a database associated with the object.

3. The method of claim 1, the contrast ratio is a relative difference between the default absorption value and the amount of light absorbed by the first portion of the object.

4. The method of claim 1, wherein the characteristic of the object is a type of the object, a shape of the object, or the material of the object.

5. The method of claim 1, wherein the characteristic of the object is indicative of whether the object includes an imperfection or a flaw.

6. The method of claim 5, wherein the imperfection or the flaw is an imperfection or a flaw of a weld of part of the object.

7. The method of claim 5, wherein:
    when the contrast ratio is above a threshold ratio the object includes the imperfection or the flaw; and
    when the contrast ratio is below the threshold ratio the object does not include the imperfection or the flaw.

8. The method of claim 1, wherein the object includes a first portion of the object that is welded to a second portion of the object.

9. The method of claim 1, further comprising applying a light absorbing compound to a surface of the object to increase the contrast ratio.

10. The method of claim 9, wherein the light absorbing compound is an infrared (IR) ink.

11. The method of claim 9, wherein the light absorbing compound is sprayed onto the surface of the object, painted onto the surface of the compound, or applied as a film on the surface of the object.

12. A method, comprising:
    illuminating, by a light source, at least a portion of a welded object, wherein the welded object is a material that absorbs or reflects a portion of the light emitted by the light source and is formed from at least two parts joined together by energy directed to the at least two parts, where a wavelength of the energy is substantially the same as a wavelength of the light transmitted from the light source;
    measuring, by a sensor, an amount of light absorbed or reflected by the welded object;
    determining, by a processing device, a contrast ratio of the absorbed or reflected light by comparing the amount of light absorbed or reflected by the welded object to a default absorption or reflection value to obtain a difference between the amount of light absorbed or reflected by the welded object and the default absorption or reflection value, wherein the contrast ratio corresponds to a weldability index representative of the absorption properties of the welded object for weldability; and
    determining, by the processing device, a characteristic of the welded object based on the contrast ratio.

13. The method of claim 12, wherein the light source is a laser emitting light having a wavelength of about one micron.

14. The method of claim 12, wherein the light source includes a back plate that reflects light emitted through a bottom of the object.

15. A system, comprising:
    a welded object formed from at least two parts joined together by energy directed to the at least two parts;
    a light source to transmit light toward the welded object, wherein a wavelength of the light transmitted from the light source is the same as a wavelength of the energy used to join the at least parts together;
    a back plate configured to reflect at least a portion of the light emitted from a bottom of the welded object;
    a light sensor to measure at least a portion of the light reflected from a joint of the welded object; and
    a processing device coupled to the light sensor, wherein the processing device is configured to:
        determine an amount of light absorbed or reflected by the welded object;
        determine a contrast ratio of the absorbed or reflected light by comparing the amount of light absorbed or reflected by the welded object to a default absorption or reflection value to obtain a difference between the amount of light absorbed or reflected by the welded object and the default absorption or reflection value, wherein the contrast ratio corresponds to a weldability index representative of the absorption properites of the welded object for weldability; and
        determine a characteristic of the welded object based on the contrast ratio.

16. The system of claim 15, wherein the contrast ratio is associated with a portion of the welded object.

17. The system of claim 15, wherein the contrast ratio is associated with an entirety of the welded object.

18. The method of claim 1, in which the object is a welded object formed from at least two parts joined together by energy directed to the at least two parts, where a wavelength of the energy is substantially the same as the wavelength of the light transmitted from the light source.

19. The method of claim 18, wherein the contrast ratio corresponds to a weldability index representative of the absorption properties of the object for weldability.

20. The method of claim 19, wherein the weldability index includes any subset range falling within a range set of 0-133 out of a scale of 0-255 such that when the weldability index falls within the subset range, the object is deemed to have an acceptable weld quality.

21. The method of claim 12, wherein the weldability index includes any subset range falling within a range set of 0-133 out of a scale of 0-255 such that when the weldability index falls within the subset range, the welded object is deemed to have an acceptable weld quality, and when the weldability index falls outside the subset range, the welded object is deemed to have an unacceptable weld quality.

22. The system of claim 15, wherein the weldability index includes any subset range falling within a range set of 0-133 out of a scale of 0-255 such that when the weldability index falls within the subset ranage, the welded object is deemed to have an acceptable weld quality, and when the weldability index falls outside the subset range, the welded object is deemed to have an unacceptable weld quality.

23. A method, comprising:
    illuminating, by a light source, a welded object, wherein:
        the light source is a laser emitting light having a wavelength of about one micron;
        the light source includes a back plate that reflects light emitted through a bottom of the welded object;
        the welded object absorbs a portion of the light emitted by the laser and is formed from at least two parts joined together by energy directed to the at least two parts, where a wavelength of the energy is substantially the same as the wavelength of the light transmitted from the light source;
    measuring, by a sensor, an amount of light absorbed by the welded object, wherein the amount of light absorbed by the object is the amount of light not reflected by the welded object
    determining, by a processing device, a contrast ratio of the absorbed light by comparing an amount of light absorbed by the welded object to a default absorption value to obtain a difference between the amount of light absorbed by the welded object and the default absorption value, wherein the contrast ratio corresponds to a weldability index representative of the absorption properties of the welded object for weldability;
    determining, by the processing device, a characteristic of the welded object based on the contrast ratio; and
    providing a notification to a user indicating the characteristic of the welded object.

24. The method of claim 23, wherein the weldability index includes any subset range falling within a range set of 0-133 out of a scale of 0-255 such that when the weldability index falls within the subset range, the welded object is deemed to have an acceptable weld quality.

25. The method of claim 23, wherein the characteristic of the object is indicative of whether the object includes an imperfection or a flaw.

26. The method of claim 25, wherein the imperfection or the flaw is an imperfection or a flaw of a weld of part of the object.

27. The method of claim 25, wherein:
    when the contrast ratio is above a threshold ratio the welded object includes the imperfection or the flaw; and
    when the contrast ratio is below the threshold ratio the welded object does not include the imperfection or the flaw.

28. The method of claim 23, further comprising applying a light absorbing compound to a surface of the object to increase the contrast ratio.

29. The method of claim 28, wherein the light absorbing compound is an infrared (IR) ink.

30. The method of claim 28, wherein the light absorbing compound is sprayed onto the surface of the welded object, painted onto the surface of the compound, or applied as a film on the surface of the welded object.

* * * * *